US009809802B2

(12) United States Patent
Solano et al.

(10) Patent No.: US 9,809,802 B2
(45) Date of Patent: Nov. 7, 2017

(54) IBV STRAINS AND USES THEREOF

(71) Applicant: BIOMUNE COMPANY, Lenexa, KS (US)

(72) Inventors: Wil Solano, Overland Park, KS (US); Brianna Ford, Lawrence, KS (US); Chris Luther, Lenexa, KS (US)

(73) Assignee: BIOMUNE COMPANY, Lenexa, KS (US)

( * ) Notice: Subject to any disclaimer, the term of this patent is extended or adjusted under 35 U.S.C. 154(b) by 0 days.

(21) Appl. No.: 14/875,171

(22) Filed: Oct. 5, 2015

(65) Prior Publication Data

US 2017/0096644 A1   Apr. 6, 2017

(51) Int. Cl.
| | | |
|---|---|---|
| *C12N 7/00* | (2006.01) | |
| *C12Q 1/70* | (2006.01) | |
| *C07K 14/005* | (2006.01) | |
| *A61K 39/00* | (2006.01) | |

(52) U.S. Cl.
CPC .............. *C12N 7/00* (2013.01); *C07K 14/005* (2013.01); *C12Q 1/701* (2013.01); *A61K 39/00* (2013.01); *C12N 2770/20021* (2013.01); *C12N 2770/20022* (2013.01); *C12N 2770/20034* (2013.01); *C12N 2770/20061* (2013.01); *C12N 2770/20071* (2013.01)

(58) Field of Classification Search
None
See application file for complete search history.

(56) References Cited

FOREIGN PATENT DOCUMENTS

WO   WO 2009143332   * 11/2009

OTHER PUBLICATIONS

Sequence alignment of instant SEQ ID No. 1 with GenEmbl database access No. KM434263 by Kulkarni et al on Aug. 29, 2014.*
Ladman et al. (Avian Pathology. 2006; 35 (2): 127-133).*
Jackwood (Avian Diseases. 2012; 56: 634-641).*
Gelb Jr., (Avian Diseases. 2013; 57: 65-70).*
Sequence alignment of SEQ ID No. 1 with geneseq database access No. AXT99622 by Sellers in WO 2009143332 on Nov. 2009.*

* cited by examiner

*Primary Examiner* — Shanon A Foley
(74) *Attorney, Agent, or Firm* — Saliwanchik, Lloyd & Eisenschenk

(57) ABSTRACT

The present invention relates to novel infectious bronchitis virus strains and the uses thereof. The invention particularly relates to an inactivated or attenuated IBV, as well as to vaccine compositions comprising the same and the uses thereof to vaccinate avians. The invention also relates to nucleic acids, infected cells and methods for detecting the infectious bronchitis virus strains of the invention in any sample.

14 Claims, No Drawings

IBV STRAINS AND USES THEREOF

The Sequence Listing for this application is Labeled "Seq-List.txt" which was created on Oct. 5, 2015 and is 7 KB. The entire content of the sequence listing is incorporated herein by reference in its entirety.

The present invention relates to novel infectious bronchitis virus strains and the uses thereof. The invention particularly relates to inactivated or attenuated IBV strains of GA08 serotype, as well as to vaccine compositions comprising the same and the uses thereof to vaccinate avians. The invention also relates to nucleic acids, infected cells and methods for detecting an infectious bronchitis virus in any sample.

BACKGROUND

Infectious bronchitis (IB) is a major disease in the poultry industry and can be associated with respiratory diseases, nephritis, fertility problems and reduced egg production or quality. The disease is caused by infectious bronchitis virus (IBV), a member of the Coronaviridae family (Cavanagh & Gelb, 2008). IBV is primarily a respiratory pathogen. The IBV genome is a single-stranded linear RNA molecule. The IBV virion contains four structural proteins, including the S glycoprotein, which is proteolytically processed into two peptides known as S1 and S2. Nucleotide sequencing of the S1 gene region is considered as the most useful technique for differentiation between distinct IBV strains and for IBV strain classification (Worthington et al., 2008).

Epidemiological studies show that different strains of IBV exist depending on the clinical manifestations and geographic regions. Various IBV strains have been isolated in the art, including, e.g., the Mass serotype, the 793B serotype, the D274 variants, the QX type or the BR type, and the GA08 or the GA13 IBV strains. Vaccination against IBV is only partially successful because of the emergence of antigenic variants and the diversity of IBV strains. Consequently, efficient vaccination requires either IBV cocktails, or the previous identification of the IBV strain prevalent in the field, and/or an IBV strain having a strong immunogenic power. Accordingly, there is a need in the art for novel IBV strains allowing the development of improved vaccines and diagnostic methods.

SUMMARY OF INVENTION

The present invention relates to novel IBV strains and the uses thereof for vaccination. The invention stems from the construction, production and selection, by the inventors, of attenuated or inactivated IBV strains having potent immunogenicity and capable of inducing cross-protective immunity to several IBV serotypes in vivo. These strains can further protect animals against renal lesions, such as nephritis, associated with some strains of IBV. The invention thus allows the development of efficient vaccines or diagnostic methods against IBV and related disorders in avians, particularly poultry.

More particularly, an object of the invention resides in an attenuated or inactivated Infectious Bronchitis Virus (IBV), wherein the virus (i) comprises an S1 gene having a nucleotide sequence with at least 95% identity to SEQ ID NO: 1 or the complementary strand thereof, and (ii) confers cross-protective immunity to at least two distinct IBV serotypes in vivo, more preferably at least 3 distinct IBV serotypes.

In a particular embodiment, the IBV of the invention can also protect vaccinated avians against renal lesions caused by IBV.

A specific example of an attenuated IBV strain of the invention is IBV 500-13 deposited at the American Type Culture Collection (ATCC), P.O. Box 1549, Manassas, Va. 20108, on Sep. 30, 2015 under Accession No. PTA-122551.

A further object of the invention is a nucleic acid comprising SEQ ID NO: 1 or a sequence having at least 95% identity to SEQ ID NO: 1, or the complementary strand thereof.

Other objects of the invention concern a vector comprising a gene sequence of an IBV as defined above under the control of a promoter, and a cell infected by an IBV as defined above or containing a vector as defined above.

The invention also residues in an S1 protein comprising SEQ ID NO: 2 or a protein having at least 95% identity to SEQ ID NO: 2.

A further object of the invention relates to a vaccine comprising an IBV as defined above and, optionally, a suitable excipient and/or adjuvant.

The invention also resides in a vaccine comprising an S1 protein, a nucleic acid or a vector as defined above and, optionally, a suitable excipient and/or adjuvant.

The invention also provides a method for vaccinating poultry against infectious bronchitis virus, comprising administering to said poultry an IBV strain or vaccine as defined above.

The invention also relates to the use of an IBV strain, protein, vector or nucleic acid as defined above for the preparation of a vaccine for use to vaccinate poultry against infectious bronchitis virus.

The invention also provides a method for protecting poultry against renal lesions, comprising administering to said poultry an IBV strain or vaccine as defined above.

The invention also relates to an IBV as defined above for use to immunize or vaccinate poultry.

The invention further provides a method for the preparation of a vaccine, comprising producing an infectious bronchitis virus as defined above in culture, harvesting the attenuated virus and processing the harvested material to produce a vaccine.

The invention also provides a method for detecting IBV in a sample, comprising contacting the sample with a probe or primer specific for an IBV sequence comprising SEQ ID NO: 1 or a sequence having 98% identity to SEQ ID NO: 1 or the complementary strand thereof, and detecting the presence of such a sequence in the sample.

DETAILED DESCRIPTION OF THE INVENTION

The present invention relates to novel IBV strains and the uses thereof, e.g., for vaccination of poultry. The invention stems from the construction, production and selection of IBV strains which are attenuated and have potent immunogenicity, being capable of inducing cross-protective immunity to several IBV serotypes in vivo and to protect against renal lesions, such as nephritis, associated with some strains of IBV. The invention thus allows the development of efficient vaccines or diagnostic methods against IBV and related disorders in avians, particularly poultry.

IBV Strains and Material

An object of the invention more particularly relates to attenuated or inactivated infectious bronchitis viruses (IBV), as well as to material derived therefrom such as nucleic acids, proteins or recombinant cells. The inventors have produced, by various attenuation treatments, isolated and characterized an IBV strain with a particular S1 gene/protein sequence (depicted as SEQ ID NOs: 1 and 2, respectively).

Such sequence has not been found in nature or in databases and is thus novel. IBVs of the invention have an attenuated phenotype as well as a very strong and cross-reactive immunogenicity. As shown in the experimental section, avians vaccinated with an IBV of the invention are protected not only against IBV of the same serotype, but also against IBV of distinct serotypes. More particularly, the results presented in the examples show that avians immunized with an IBV of the invention are protected from infectious diseases caused by IBV of serotypes GA08, GA13 or DMV. Such cross-protective attenuated IBV had never been reported in the literature and confers remarkable advantages in terms of protection. Moreover, the results obtained also demonstrate that IBVs of the invention can protect vaccinated birds against renal lesions caused by IBVs, which represents a further advantage of the invention. Also, by sequence alignment and neutralization tests, the inventors have determined that the IBV strains of the invention belong essentially to GA08 serotype.

An object of the invention thus resides in an attenuated or inactivated Infectious Bronchitis Virus (IBV), wherein the virus (i) comprises an S1 gene having a nucleotide sequence with at least 95% identity to SEQ ID NO: 1, or the complementary strand thereof and (ii) confers cross-protective immunity to at least two distinct IBV serotypes in vivo, more preferably at least 3 distinct IBV serotypes.

The degree of homology between two amino acid or nucleic acid sequences may be determined by means of computer programs known per se in the art, such as GAP, provided in the GCG program package (Program Manual for the Wisconsin Package, Version 8, August 1996, Genetics Computer Group, 575 Science Drive, Madison, Wis., USA 53711) (Needleman, S. B. and Wunsch, C. D. (1970), Journal of Molecular Biology, 48, 443-453). GAP is used with the following settings for DNA sequence comparison: GAP creation penalty of 5.0 and GAP extension penalty of 0.3. Nucleic acid/amino acid molecules may be aligned to each other using the Pileup alignment software, available as part of the GCG program package, using, for instance, the default settings of gap creation penalty of 5 and gap width penalty of 0.3. Typically, the degree of identity is measured over the entire length of the compared sequence.

Preferably, the attenuated IBV of the invention comprises an S1 gene having a nucleotide sequence with at least 96% identity to SEQ ID NO: 1, or the complementary strand thereof, even more preferably at least 97%, at least 98%, or at least 99%.

In a particular embodiment, the attenuated IBV of the invention comprises an S1 gene having the nucleic acid sequence of SEQ ID NO: 1.

```
ATGTTGGGGAAGTCACTGTTTTTAGTGACCATTTTGTTTGCACTATGTA

GTGCTAATTTATATGATAATAATTCTTTTGTGTATTACTACCAGAGTGC

TTTTAGGCCAGGACATGGTTGGCATTTACATGGAGGTGCTTATGCAGTA

GTTAATGTGTCTAGTGAAAATAATAATGCAGGTACTGCCCAAAGTTGCA

CTGCTGGTGCTATTGGCTACAGTAAGAATCTCAGTGCGGCCTCAGTAGC

CATGACTGCACCACTAAGTGGTATGTCATGGTCTGTAAACCAATTTTGT

ACGGCTCACTGCAATTTTACTAGTTTTACAGTGTTTGTTACACATTGTT

TTAAGTCAGGTGCCAAGGAGTGTCCTTTGACTGGTTTCATTCAAAAGGG

TTATCTTCGCATTGCCGCTATGAAACAAAACGGTAGTGGGCCTGCTGAC
```

-continued

```
TTATTTTATAATTTAACAGTTCCAGTGACTAAATACCCTGTGTTTAGAT

CACTTCAATGTGTTAATAATCAAACATCTGTATATTTAAATGGTGATCT

TGTTTTTACTTCTAATGAGACTATTGATGTCTCAGGTGCTGGTGTTTAT

TTTAAAGCTGGTGGACCTATAACTTATAAAGTTATGAGAGAAGTAAAAG

CTTTGGCTTATTTTGTTAATGGTACTGCACAAGATGTTATTCTCTGTGA

TGAATCACCTAGAGGTTTGTTAGCATGCCAATATAATACTGGCAATTTT

TCAGATGGCTTCTATCCTTTTACTAATTCTAGTTTAGTTAAGGAAAAGT

TTATTGTTTATCGTGAGAATAGTATTAATACCACTTTGGTTTTACATAA

TTTTACGTTTCATAATGAAAGCAATGCACAACCTAATCTTGGTGGTGTT

AATAACATTGCCATTTATCAAACACAAACAGCTCAGAGTGGCTATTATA

ATTTTAATTTCTCATTTCTGAGTAGTTTTGTTTATAAGCCAAGTGATTT

TATGTATGGGTCTTTTCACCCACAGTGTAGTTTTAGACCAGAAAACATT

AATAATGGGCTCTGGTTCAATTCACTTTCAATTTCACTTGCTTACGGCC

CACTACAAGGGGGCTGTAAACAGTCAGTTTTTAGTCGCAAAACAACGTG

TTGTTATGCTTATTCATATGGCGGTCCTCATTTGTGTAAAGGTGTTTAT

GCAGGTGAGTTAACAAAGAATTTTGAGTGTGGCTTGTTAGTTTATATTA

CTAAGAGTGATGGTTCTCGTATACAAACGGCAACAGAAGCACCTGTAGT

AACCACAAATTTTTACAATAACATTACTTTGAATAAGTGTGTTGAGTAT

AATATATACGGTAGAATTGGCCAAGGTTTTATTACTAATGTAACTGATT

TAGCTTCTAGTTACAATTATTTGGCAGACGGTGGACTAGCTATTTTAGA

CACATCTGGTGCCATAGATATCTTCGTTGTACAAGGTGAATATGGTTTT

AATTATTATAAGGTTAACCCTTGTGAAGATGTTAACCAACAGTTTGTAG

TGTCAGGTGGTAATATAGTTGGCATTCTTACTTCACGTAATGAAACTGG

TTCTCAGCCTCTTGAAAATCAGTTTTATATTAAGTTAACTAATGG
```

The sequence of the encoded S1 protein is depicted below, as SEQ ID NO: 2.

```
MLGKSLFLVTILFALCSANLYDNNSFVYYYQSAFRPGHGWHLHGGAYAV

VNVSSENNNAGTAQSCTAGAIGYSKNLSAASVAMTAPLSGMSWSVNQFC

TAHCNFTSFTVFVTHCFKSGAKECPLTGFIQKGYLRIAAMKQNGSGPAD

LFYNLTVPVTKYPVFRSLQCVNNQTSVYLNGDLVFTSNETIDVSGAGVY

FKAGGPITYKVMREVKALAYFVNGTAQDVILCDESPRGLLACQYNTGNF

SDGFYPFTNSSLVKEKFIVYRENSINTTLVLHNFTFHNESNAQPNLGGV

NNIAIYQTQTAQSGYYNFNFSFLSSFVYKPSDFMYGSFHPQCSFRPENI

NNGLWFNSLSISLAYGPLQGGCKQSVFSRKTTCCYAYSYGGPHLCKGVY

AGELTKNFECGLLVYITKSDGSRIQTATEAPVVTTNFYNNITLNKCVEY

NIYGRIGQGFITNVTDLASSYNYLADGGLAILDTSGAIDIFVVQGEYGF

NYYKVNPCEDVNQQFVVSGGNIVGILTSRNETGSQPLENQFYIKLTNG
```

In a particular embodiment, the invention relates to an attenuated IBV having an S1 gene sequence comprising SEQ ID NO: 1 or the complementary strand thereof.

As indicated above, IBVs of the invention have a remarkable property of conferring cross-protective immunity to at least two distinct IBV serotypes in vivo, more preferably at least 3 distinct serotypes in vivo. In this regard, in a preferred embodiment, the IBV of the invention confers cross-protective immunity against at least 2 IBV serotypes selected from GA08, GA13 and DMV IBV serotypes.

In a more particular embodiment, the IBV of the invention confers protective immunity against GA08 and GA13 IBV serotypes in vivo.

In another particular embodiment, the IBV of the invention confers protective immunity against GA08 and DMV IBV serotypes in vivo.

In a further preferred embodiment, the IBV of the invention confers cross-protective immunity against GA08, GA13 and DMV IBV serotypes in vivo.

The ability to confer protective immunity against an IBV serotype indicates that at least 75% of avians vaccinated with the IBV strain will be protected against disease caused by at least one strain of such serotype. In this regard, the experimental section shows that almost 90% of avians vaccinated with an IBV of the invention were protected against subsequent challenge with a GA13 or DMV IBV strain, and up to 100% were protected against subsequent challenge with a GA08 IBV strain. Such a potent cross-protective immunity is remarkable and confers unique advantages to the IBV strains of this invention.

Also, a further remarkable advantage of preferred IBVs of the invention is their ability to protect vaccinated avians also against renal lesions caused by nephropathogenic IBVs, in particular nephritis. In this regard, the invention shows that, in response to a challenge with a nephropathogenic IBV strain, birds vaccinated according to the invention essentially did not develop any renal lesions such as interstitial nephritis or foci of interstitial lymphocytes in kidney tissue. In contrast, placebo groups developed such nephritis, including confluent to large foci of interstitial lymphocytes, which are representative of severe nephritis. The invention thus allows the prevention, reduction or inhibition of development of renal lesions or nephritis following infection by a nephropathogenic IBV. Such prevention includes any reduction by at least 20%, preferably at least 50%, 80%, 100% or more, of the extent of such renal lesions as compared to untreated avians.

The most preferred and advantageous IBV strains of the invention are thus attenuated IBV which (i) comprises an S1 gene having a nucleotide sequence with at least 95% identity to SEQ ID NO: 1, or the complementary strand thereof, (ii) confers cross-protective immunity to at least two distinct IBV serotypes in vivo selected from GA08, GA13 and DMV and (iii) reduces renal lesions caused by a nephropathogenic IBV, such as a DMV.

A specific example of an attenuated IBV strain according to the invention is IBV 500-13, which was deposited on Sep. 30, 2015 at the ATCC under Accession No. PTA-122551.

The IBV viruses of the invention are attenuated, i.e., they are live viruses which retain immunogenic properties but are devoid of at least 70%, preferably at least 80%, even more preferably at least 90% of pathogenic properties or virulence. An attenuated virus can thus induce an immune response that protects the bird against a non-attenuated strain (i.e., a natural virulent strain) but that does not by itself cause substantial illness to the bird. In a preferred embodiment, the attenuated character indicates that the viruses, upon in vivo administration, do not cause illness to avians.

From the attenuated viruses of the invention, the skilled artisan may prepare inactivated or killed IBV preparations. Preparation of an inactivated IBV may be obtained by chemical or physical means. Chemical inactivation can be effected by treating the IBV strain with enzymes, formaldehyde, β-propiolactone, binary ethylenimine or a derivative thereof. The inactivated IBV so obtained may be neutralized or stabilized afterwards. Physical inactivation may be carried out by subjecting the IBV strain to energy-rich radiation, such as UV light, X-radiation or γ-radiation.

A particular object of the invention thus relates to an inactivated IBV obtainable by inactivating an IBV of the invention as defined above.

IBVs of the invention may be cultured, produced, expanded or maintained using conventional culture techniques. In particular, the virus may be used to infect competent cells in vitro or in vivo, and the virus may be collected upon replication or amplification. Competent cells include CEF, (SPF) embryonated eggs, chicken kidney cells, and the like. The cells or viruses may be cultured in a culture medium such as Eagle's MEM or Leibowitz-L-15/McCoy 5A (1:1 mixture) culture medium at about 37° C. for 3 to 6 days. The infected cells are typically suspended in a culture medium containing 10% dimethyl sulfoxide (DMSO) and stored frozen under liquid nitrogen. The virus may be collected using conventional techniques (filtration, precipitation, chromatography, etc.) and stored either in liquid, lyophilized or frozen stage. Inactivation is generally performed after production.

A further object of the invention is a cell infected by an IBV as defined above.

The invention also relates to a nucleic acid molecule comprising SEQ ID NO: 1 or a sequence having at least 99% identity to SEQ ID NO: 1, or the complementary strand thereof.

The invention further concerns a vector (e.g., a plasmid, recombinant virus, phage, etc.) comprising a gene sequence of an IBV as defined above under the control of a promoter. A preferred gene sequence is an S1 sequence.

The invention also relates to a protein comprising SEQ ID NO: 2 or a sequence having at least 99% identity to SEQ ID NO: 2.

Compositions and Vaccines

The invention also concerns a vaccine or composition comprising an IBV, nucleic acid, vector or protein of the invention and, optionally, a suitable excipient and/or adjuvant.

A particular composition or vaccine of the invention comprises an IBV strain and, optionally, a suitable excipient and/or adjuvant. Typically, vaccines of the invention comprise an effective amount of at least one IBV strain, such as preferably from 1.0E2.0 to 1.0E5.0 EID50/dose, more preferably from 1.0E2.0 EID50/dose to 1.0E3.0 EID50/dose. Each vaccine preferably contains a unitary dose sufficient to elicit a protective immune response in avian species, which may be determined by known methods using, e.g., antigen/anti-body reactions, for example by the ELISA method.

The vaccines and compositions according to the present invention may comprise any suitable excipient such as a solvent, diluent, carrier, stabilizer or the like. Examples of excipients include, for example, an aqueous buffer or a phosphate buffer, a physiological saline (0.85%), phosphate-buffered saline (PBS), citrate buffers, Tris(hydroxymethyl aminomethane (TRIS), Tris-buffered saline and the like.

Preferably, the vaccines also comprise an adjuvant. Adjuvants may be obtained from any source including proteins and peptides derived from animals (e.g., hormones, cytokines, co-stimulatory factors), nucleic acids derived from viruses and other sources (e.g., double-stranded RNA, CpG), aluminum hydroxide, plant extracts, and the like, and are administered with the vaccine in an amount sufficient to enhance the immune response.

The vaccines or compositions of the invention may further comprise or may be used in combination with other avian vaccines or antigens, for example Newcastle Disease Virus (NDV), Infectious Bursal Disease, and/or other IBV serotypes, or antigens derived therefrom.

Methods and Vaccination

The IBV viruses and material of the invention may be used to induce protective immunity in avians, particularly poultry, or to treat IBV-infected avians, particularly poultry. The invention is particularly suited to vaccinate poultry prior to IBV infection, in a preventive setting.

The invention thus also relates to an IBV virus or nucleic acid or protein or vaccine as defined above, for use to immunize or vaccinate poultry.

The invention also concerns the use of an IBV virus or nucleic acid or protein as defined above for the preparation of a vaccine for use to vaccinate poultry against infectious bronchitis virus.

The invention also relates to a method for protecting an avian, preferably a poultry, more particularly a chicken, against infectious bronchitis virus, comprising administering to said avian an IBV virus, nucleic acid, protein or vaccine as defined above.

The invention also relates to a method for inducing an IBV immunity in an avian, preferably a poultry, more particularly a chicken, comprising administering to said avian an IBV virus, nucleic acid, protein or vaccine as defined above.

The invention also relates to a method for protecting an avian, preferably a poultry, more particularly a chicken, against renal lesions caused by an IBV, comprising administering to said avian an IBV virus, nucleic acid, protein or vaccine as defined above.

The invention also relates to a method for inducing an immunity against several IBV serotypes in an avian, preferably a poultry, more particularly a chicken, comprising administering to said avian an IBV virus, nucleic acid, protein or vaccine as defined above.

The route of administration can be any route including oral, ocular (e.g., by eyedrop), oculo-nasal administration using aerosol, intranasal, cloacal, in feed, in water, or by spray and gel spray, in ovo, topically, or by injection (e.g., intravenous, subcutaneous, intramuscular, intraorbital, intraocular, intradermal, and/or intraperitoneal). The vaccines of the invention can be administered as single doses or in repeated doses, depending on the vaccination protocol. Also, administration can be made at any age depending on the conditions, for instance in ovo and from day one up to between 10 to 20 weeks of age.

The results presented in the experimental section show that vaccination with an IBV of the invention can cause protection of avians against diseases caused by IBVs of serotype GA08, GA13 or DMV. As shown, depending on administration route, up to 100% of vaccinated avians were protected against challenge by a serotype GA08 IBV. Furthermore, nearly 90% of vaccinated avians were protected against challenge by a serotype GA13 or DMV IBV. Such results illustrate the unexpected potent cross-immunogenicity of the IBVs of the invention.

The invention also relates to methods for detecting IBV in a sample, comprising contacting the sample with a probe or primer specific for an IBV sequence comprising SEQ ID NO: 1 or a sequence having 99% identity to SEQ ID NO: 1 or the complementary strand thereof, and detecting the presence of such a sequence in the sample.

Further aspects and advantages of the invention will be disclosed in the following experimental section.

EXAMPLES

Example 1: Genetic Analysis of IBV 500-13

500-13 was prepared by culture on avian cells. The nucleic acid was isolated and sequenced. The sequence of the S1 gene is presented in SEQ ID NO: 1. Sequence alignment confirmed that this sequence does not exist in nature and is not found in databases. Various tests also confirmed that 500-13 is attenuated and does not cause disease in avians. A sample of 500-13 was deposited on Sep. 30, 2015 at ATCC under Accession No. PTA-122551.

The method of Archetti and Horsfall (Journal of Experimental Medicine 92 (1950) 441) was used for calculating antigenic relatedness ("r") values of virus neutralization tests. The results obtained gave an r value of 86% with the GA08 IBV strain, showing that 500-13 belongs to serotype GA08.

Example 2: Effective Protection In Vivo Against Challenge with Live Virulent GA08 IBV The present example shows that attenuated IBV 500-13 of the invention can confer strong protective immunity in vivo against an IBV strain of the GA08 serotype.

Protocol

| Event | Time Relative to Event (age) |
|---|---|
| Hatch and Vaccinate | 0 days of age |
| Challenge | 26 days of age |
| Necropsy | 5 dpc (31 days of age) |

Vaccination was performed with 1.0E2.8 and 1.0E3.1 EID50 per 0.2 ml of 500-13. Placebo was composed of $H_2O$, 0.2 mL. Each bird received 0.2 mL of vaccine by coarse spray. Challenge was made with 1.0E3.5 EID50/ml of live GA08 IBV by intraocular (TO) administration.

Results

| Treatment | Virus Isolation as # negative/total # (% protected) |
|---|---|
| 500-13 – 1.0E3.1 dose | 26/30 (87%) |
| 500-13 – 1.0E2.8 dose | 27/30 (90%) |
| placebo-vaccinated, challenged controls | 1/30 (3%) |

These results demonstrate the efficacy of 500-13 vaccine containing as low as 1.0E2.8 EID50/dose IBV. Indeed, up to 90% of vaccinated chickens were protected against the IBV GA08 type homologous challenge.

Example 3: Effective Protection In Vivo Against Challenge with Live Virulent GA13 IBV The present example shows that an attenuated IBV of the invention can confer strong protective immunity in vivo against GA13, a live virulent IBV of a different serotype.

Protocol

| Event | Time Relative to Event (age) |
|---|---|
| Hatch and Vaccinate | 0 days of age |
| Challenge | 28 days of age |
| Necropsy | 5 dpc (33 days of age) |

Vaccination was performed with 1.0E2.8 EID50 per 0.2 ml of 500-13. Placebo was composed of $H_2O$, 0.2 mL. Each bird received 0.2 mL of vaccine by coarse spray. Challenge was made with 1.0E4.7 EID50/ml of live GA13 IBV by IO administration.

Results

| Treatment | Virus Isolation as # negative/total # (% protected) |
|---|---|
| 500-13 – 1.0E2.8 dose | 26/30 (87%) |
| placebo-vaccinated, challenged controls | 0/30 (0%) |

These results demonstrate the efficacy and cross-protective immunity of 500-13 vaccine. Indeed, up to 87% of vaccinated chickens were protected against the IBV challenge with heterologous GA13.

Example 4: Effective Protection In Vivo Against Challenge with Live Virulent DMV IBV The present example shows that an attenuated IBV of the invention can confer strong protective immunity in vivo against DMV/1639/11, a live virulent IBV of a different serotype.

Protocol

| Event | Time Relative to Event (age) |
|---|---|
| Hatch and Vaccinate | 0 days of age |
| Challenge | 28 days of age |
| Necropsy | 5 dpc (33 days of age) |

Vaccination was performed with 1.0E3.0 EID50 per 0.2 ml of 500-13. Placebo was composed of $H_2O$, 0.2 mL. Each bird received 0.2 mL of vaccine by coarse spray. Challenge was made with 1.0E4.0 EID50/ml of live IBV variant DMV/1639/11 by IO administration.

Results

| Treatment | Virus Isolation as # negative/total # (% protected) |
|---|---|
| 500-13 – 1.0E3.0 dose | 26/30 (87%) |
| placebo-vaccinated, challenged controls | 0/30 (0%) |

These results demonstrate the efficacy and cross-protective immunity of 500-13 vaccine. Indeed, up to 87% of vaccinated chickens were protected against the IBV challenge with heterologous DMV.

Example 5: Comparison Between 500-13 and Other IBV Strains

Broiler chickens were vaccinated by intratracheal route with an IBV strain of the invention (500-13) or comparative attenuated IBV strains derived from GA-13 or GA-08. The chickens were then subjected to an ocular and intranasal challenge with IBV (strain DMV/1639/11) at 4 weeks of age. The results are disclosed below:

| IBV Vaccination (1 Day + 10 Days) | No. of Birds | IBV (DMV/1639/11) Challenge at 4 Weeks[4] % Protection |
|---|---|---|
| 500-13 ($10^{3.8}$ $EID_{50}$ per dose) | 20 | >80% |
| GA13 ($10^{4.5}$ $EID_{50}$ per dose) | 20 | <30% |
| GA08 ($10^{5.3}$ $EID_{50}$ per dose) | 20 | <20% |
| None (Challenge Controls) | 10 | 0% |

[4]IBV (DMV/1639/11) challenge = $10^{3.2}$ $EID_{50}$ per bird

These results confirm the ability of 500-13 to confer cross-protective immunity against a distinct IBV serotype (namely DMV). In contrast, GA13 or GA08 vaccinated animals were not protected against challenge with DMV.

Example 6: Oral Vaccination with 500-13 Induces Protective Immunity

In this example, chickens at 1 day of age were vaccinated by gel drops with 1.0E2.8 EID50/0.25 mL dose of 500-13. All vaccinated chicks were allowed five minutes to preen the gel from each other and then transferred to an isolator. At 27 days post-vaccination (dpv), chicks were challenged with 1.0E3.2 EID50/0.06 mL dose of IBV (GA08), a virulent IBV strain of the same serotype as 500-13. Protection of chickens against disease was assessed at Day 5 post-challenge. The results are shown below:

| Vx ID | No. Birds/Group | # Pos | % Pos | % Neg |
|---|---|---|---|---|
| 500-13 | 30 | 0 | 0 | 100 |
| Placebo | 30 | 29 | 97 | 3 |

The results show that 500-13 administered by oral gel drop vaccination conferred 100% protection against IBV to the chickens.

Example 7: 500-13 Protects Vaccinated Birds from Renal Lesions

The present example shows that an attenuated IBV of the invention can prevent or inhibit development of renal lesions in vaccinated birds.

SPF chickens were used. Vaccination was performed at day 0 with 1.0E3.0 EID50 per 0.2 ml of 500-13 (group A). Placebo was composed of $H_2O$, 0.2 mL (group B). Each bird received 0.2 mL of vaccine by coarse spray. At 4 weeks, a challenge was made with 1.0E4.0 EID50/ml of live IBV variant DMV/1639/11 by IO administration. At 6 weeks, the kidneys from the vaccinated and placebo groups were collected and submitted as formalin fixed tissue. Several sections of each kidney were prepared for examination. Tissues were examined histologically and lesions identified and scored as: 1, normal (no evidence of interstitial nephritis); 2, mild (small focus of interstitial lymphocytes); 3, moderate (scattered small foci of interstitial lymphocytes); and 4, marked to severe (locally extensive to confluent large foci of interstitial lymphocytes).

The lesion scores were recorded and are provided in the following table. For each group, a mean score of interstitial nephritis was calculated.

Results

The results are presented in the following tables:

| Group A | | | | | | | | | | | | | | | |
|---|---|---|---|---|---|---|---|---|---|---|---|---|---|---|---|
| sections | 1 | 2 | 3 | 4 | 5 | 6 | 7 | 8 | 9 | 10 | 11 | 12 | 13 | 14 | 15 | Mean score |
| Intersitial nephritis score | 3 | 2 | 1 | 1 | 1 | 2 | 1 | 1 | 1 | 1 | 3 | 1 | 1 | 1 | 1 | 1.4 |

| Group B | | | | | | | | | | | | | | | |
|---|---|---|---|---|---|---|---|---|---|---|---|---|---|---|---|
| sections | 1 | 2 | 3 | 4 | 5 | 6 | 7 | 8 | 9 | 10 | 11 | 12 | 13 | 14 | 15 | Mean score |
| Intersitial nephritis score | 4 | 3 | 1 | 4 | 1 | 4 | 4 | 2 | 1 | 3 | 2 | 4 | 1 | 3 | 4 | 2.73 |

They show that vaccinated animals had a mean lesion score of 1.4, while the non-vaccinated animals had a mean lesion score of 2.73. Lesions in the non-vaccinated group comprised focal to coalescing foci of lymphocytic inflammation in the interstitial tissue of the kidneys. The results of this example illustrate a strong protective effect of the IBV of the present invention.

We claim:

1. An attenuated Infectious Bronchitis Virus (IBV), wherein said IBV (i) comprises a S1 gene having a nucleotide sequence with at least 99% identity to SEQ ID NO: 1, or the complementary strand thereof and (ii) confers protective immunity to at least two IBV serotypes selected from GA08, GA13 and DMV.

2. The IBV of claim 1, wherein said IBV confers protective immunity to IBV serotypes GA08, GA13 and DMV.

3. The IBV of claim 1, wherein said IBV protects against renal lesions.

4. An attenuated Infectious bronchitis virus (IBV) of claim 1, wherein said IBV:
   (i) comprises a S1 gene comprising the nucleotide sequence of SEQ ID NO: 1, or the complementary strand thereof, and
   (ii) confers protective immunity to at least 2 IBV serotypes selected from GA08, GA13 and DMV.

5. A cell containing an IBV of claim 1.

6. The IBV of claim 1, which is IBV 500-13 deposited at ATCC under No. PTA-122551.

7. An inactivated IBV obtainable by inactivating an IBV of claim 1.

8. A vaccine comprising an IBV of claim 1 and, optionally, a suitable excipient and/or adjuvant.

9. A method for vaccinating poultry against infectious bronchitis virus comprising administering a vaccine of claim 8 to said poultry.

10. The method of claim 9, for inducing protective immunity to poultry against at least 2 IBV serotypes selected from GA08, GA13 and DMV serotypes.

11. A method for the preparation of a vaccine comprising producing an infectious bronchitis virus according to claim 1 in culture, harvesting the attenuated virus and processing the harvested material to produce a vaccine.

12. A nucleic acid comprising SEQ ID NO: 1 or a sequence having at least 99% identity to SEQ ID NO: 1, or the complementary strand thereof.

13. A vector comprising SEQ ID NO: 1, or a sequence having at least 99% sequence identity to SEQ ID NO: 1, under the control of a promoter.

14. A cell containing a vector of claim 13.

* * * * *

UNITED STATES PATENT AND TRADEMARK OFFICE
CERTIFICATE OF CORRECTION

PATENT NO. : 9,809,802 B2
APPLICATION NO. : 14/875171
DATED : November 7, 2017
INVENTOR(S) : Wil Solano, Brianna Ford and Chris Luther Page 1 of 1

It is certified that error appears in the above-identified patent and that said Letters Patent is hereby corrected as shown below:

In the Specification

Column 8,
Line 45, "by intraocular (TO)" should read --by intraocular (IO)--.

Signed and Sealed this
Twenty-fourth Day of July, 2018

Andrei Iancu
*Director of the United States Patent and Trademark Office*

```
                        SEQUENCE LISTING

<160> NUMBER OF SEQ ID NOS: 2

<210> SEQ ID NO 1
<211> LENGTH: 1613
<212> TYPE: DNA
<213> ORGANISM: Artificial
<220> FEATURE:
<223> OTHER INFORMATION: S1 gene sequence

<400> SEQUENCE: 1
atgttgggga agtcactgtt tttagtgacc attttgtttg cactatgtag tgctaattta      60
tatgataata attcttttgt gtattactac cagagtgctt ttaggccagg acatggttgg     120
catttacatg gaggtgctta tgcagtagtt aatgtgtcta gtgaaaataa taatgcaggt     180
actgcccaaa gttgcactgc tggtgctatt ggctacagta agaatctcag tgcggcctca     240
gtagccatga ctgcaccact aagtggtatg tcatggtctg taaaccaatt ttgtacggct     300
cactgcaatt ttactagttt tacagtgttt gttacacatt gttttaagtc aggtgccaag     360
gagtgtcctt tgactggttt cattcaaaag ggttatcttc gcattgccgc tatgaaacaa     420
aacggtagtg ggcctgctga cttattttat aatttaacag ttccagtgac taaatacct      480 gtgtttagat cacttcaatg tgttaataat caaacatctg tatatttaaa tggtgatctt     540
gtttttactt ctaatgagac tattgatgtc tcaggtgctg gtgtttattt taaagctggt     600
ggacctataa cttataaagt tatgagagaa gtaaaagctt tggcttattt tgttaatggt     660
actgcacaag atgttattct ctgtgatgaa tcacctagag gtttgttagc atgccaatat     720
aatactggca atttttcaga tggcttctat cctttactaa attctagttt agttaaggaa     780
aagtttattg tttatcgtga gaatagtatt aataccactt tggttttaca taattttacg     840
tttcataatg aaagcaatgc acaacctaat cttggtggtg ttaataacat tgccatttat     900
```

-continued

```
caaacacaaa cagctcagag tggctattat aattttaatt tctcatttct gagtagtttt    960
gtttataagc caagtgattt tatgtatggg tcttttcacc cacagtgtag ttttagacca   1020
gaaaacatta ataatgggct ctggttcaat tcactttcaa tttcacttgc ttacggccca   1080
ctacaagggg gctgtaaaca gtcagttttt agtcgcaaaa caacgtgttg ttatgcttat   1140
tcatatggcg gtcctcattt gtgtaaaggt gtttatgcag gtgagttaac aaagaatttt   1200
gagtgtggct tgttagttta tattactaag agtgatggtt ctcgtataca aacggcaaca   1260
gaagcacctg tagtaaccac aaatttttac aataacatta ctttgaataa gtgtgttgag   1320
tataatatat acggtagaat tggccaaggt tttattacta atgtaactga tttagcttct   1380
agttacaatt atttggcaga cggtggacta gctattttag acacatctgg tgccatagat   1440
atcttcgttg tacaaggtga atatggtttt aattattata aggttaaccc ttgtgaagat   1500
gttaaccaac agtttgtagt gtcaggtggt aatatagttg gcattcttac ttcacgtaat   1560
gaaactggtt ctcagcctct tgaaaatcag ttttatatta agttaactaa tgg          1613
```

<210> SEQ ID NO 2
<211> LENGTH: 538
<212> TYPE: PRT
<213> ORGANISM: Artificial
<220> FEATURE:
<223> OTHER INFORMATION: S1 protein sequence

<400> SEQUENCE: 2

```
Met Leu Gly Lys Ser Leu Phe Leu Val Thr Ile Leu Phe Ala Leu Cys
1               5                   10                  15

Ser Ala Asn Leu Tyr Asp Asn Asn Ser Phe Val Tyr Tyr Tyr Gln Ser
            20                  25                  30

Ala Phe Arg Pro Gly His Gly Trp His Leu His Gly Gly Ala Tyr Ala
        35                  40                  45

Val Val Asn Val Ser Ser Glu Asn Asn Asn Ala Gly Thr Ala Gln Ser
    50                  55                  60

Cys Thr Ala Gly Ala Ile Gly Tyr Ser Lys Asn Leu Ser Ala Ala Ser
65                  70                  75                  80

Val Ala Met Thr Ala Pro Leu Ser Gly Met Ser Trp Ser Val Asn Gln
                85                  90                  95

Phe Cys Thr Ala His Cys Asn Phe Thr Ser Phe Thr Val Phe Val Thr
            100                 105                 110

His Cys Phe Lys Ser Gly Ala Lys Glu Cys Pro Leu Thr Gly Phe Ile
        115                 120                 125

Gln Lys Gly Tyr Leu Arg Ile Ala Ala Met Lys Gln Asn Gly Ser Gly
    130                 135                 140

Pro Ala Asp Leu Phe Tyr Asn Leu Thr Val Pro Val Thr Lys Tyr Pro
145                 150                 155                 160

Val Phe Arg Ser Leu Gln Cys Val Asn Asn Gln Thr Ser Val Tyr Leu
                165                 170                 175

Asn Gly Asp Leu Val Phe Thr Ser Asn Glu Thr Ile Asp Val Ser Gly
            180                 185                 190

Ala Gly Val Tyr Phe Lys Ala Gly Gly Pro Ile Thr Tyr Lys Val Met
        195                 200                 205

Arg Glu Val Lys Ala Leu Ala Tyr Phe Val Asn Gly Thr Ala Gln Asp
    210                 215                 220

Val Ile Leu Cys Asp Glu Ser Pro Arg Gly Leu Leu Ala Cys Gln Tyr
225                 230                 235                 240
```

```
Asn Thr Gly Asn Phe Ser Asp Gly Phe Tyr Pro Phe Thr Asn Ser Ser
                245                 250                 255

Leu Val Lys Glu Lys Phe Ile Val Tyr Arg Glu Asn Ser Ile Asn Thr
            260                 265                 270

Thr Leu Val Leu His Asn Phe Thr Phe His Asn Glu Ser Asn Ala Gln
            275                 280                 285

Pro Asn Leu Gly Gly Val Asn Asn Ile Ala Ile Tyr Gln Thr Gln Thr
        290                 295                 300

Ala Gln Ser Gly Tyr Tyr Asn Phe Asn Phe Ser Phe Leu Ser Ser Phe
305                 310                 315                 320

Val Tyr Lys Pro Ser Asp Phe Met Tyr Gly Ser Phe His Pro Gln Cys
                325                 330                 335

Ser Phe Arg Pro Glu Asn Ile Asn Asn Gly Leu Trp Phe Asn Ser Leu
            340                 345                 350

Ser Ile Ser Leu Ala Tyr Gly Pro Leu Gln Gly Gly Cys Lys Gln Ser
        355                 360                 365

Val Phe Ser Arg Lys Thr Thr Cys Cys Tyr Ala Tyr Ser Tyr Gly Gly
    370                 375                 380

Pro His Leu Cys Lys Gly Val Tyr Ala Gly Glu Leu Thr Lys Asn Phe
385                 390                 395                 400

Glu Cys Gly Leu Leu Val Tyr Ile Thr Lys Ser Asp Gly Ser Arg Ile
            405                 410                 415

Gln Thr Ala Thr Glu Ala Pro Val Val Thr Thr Asn Phe Tyr Asn Asn
        420                 425                 430

Ile Thr Leu Asn Lys Cys Val Glu Tyr Asn Ile Tyr Gly Arg Ile Gly
        435                 440                 445

Gln Gly Phe Ile Thr Asn Val Thr Asp Leu Ala Ser Ser Tyr Asn Tyr
    450                 455                 460

Leu Ala Asp Gly Gly Leu Ala Ile Leu Asp Thr Ser Gly Ala Ile Asp
465                 470                 475                 480

Ile Phe Val Val Gln Gly Glu Tyr Gly Phe Asn Tyr Tyr Lys Val Asn
            485                 490                 495

Pro Cys Glu Asp Val Asn Gln Gln Phe Val Val Ser Gly Gly Asn Ile
            500                 505                 510

Val Gly Ile Leu Thr Ser Arg Asn Glu Thr Gly Ser Gln Pro Leu Glu
        515                 520                 525

Asn Gln Phe Tyr Ile Lys Leu Thr Asn Gly
        530                 535
```